(12) United States Patent
Tanaka et al.

(10) Patent No.: US 8,222,193 B2
(45) Date of Patent: Jul. 17, 2012

(54) HYDROGEL PARTICLES

(75) Inventors: Kimitaka Tanaka, Wakayama (JP); Satoshi Ueno, Wakayama (JP); Koji Mine, Wakayama (JP)

(73) Assignee: Kao Corporation, Tokyo (JP)

( * ) Notice: Subject to any disclaimer, the term of this patent is extended or adjusted under 35 U.S.C. 154(b) by 165 days.

(21) Appl. No.: 12/307,294

(22) PCT Filed: Jun. 26, 2007

(86) PCT No.: PCT/JP2007/063194
§ 371 (c)(1), (2), (4) Date: Jan. 2, 2009

(87) PCT Pub. No.: WO2008/010402
PCT Pub. Date: Jan. 24, 2008

(65) Prior Publication Data
US 2009/0312213 A1      Dec. 17, 2009

(30) Foreign Application Priority Data

Jul. 20, 2006  (JP) .................................. 2006-198288
Oct. 2, 2006  (JP) .................................. 2006-270855

(51) Int. Cl.
  *C11D 3/14*   (2006.01)
(52) U.S. Cl. ........ 510/139; 510/119; 510/130; 510/132; 510/138; 510/395; 510/418; 510/422; 510/438
(58) Field of Classification Search ................ 510/119, 510/130, 132, 138, 139, 395, 418, 422, 438
  See application file for complete search history.

(56) References Cited

U.S. PATENT DOCUMENTS

| | | | | |
|---|---|---|---|---|
| 4,141,766 | A | * | 2/1979 | Cameron et al. .................... 149/2 |
| 4,155,870 | A | * | 5/1979 | Jorgensen ...................... 510/139 |
| 5,145,685 | A | * | 9/1992 | Carmody ...................... 424/501 |
| 5,900,578 | A | * | 5/1999 | Wathen ......................... 102/313 |
| 6,106,815 | A | * | 8/2000 | Kang et al. ................. 424/70.12 |
| 2001/0038831 | A1 | * | 11/2001 | Park et al. ................... 424/78.31 |
| 2004/0191330 | A1 | * | 9/2004 | Keefe et al. ..................... 424/638 |
| 2005/0043653 | A1 | * | 2/2005 | Trimmer et al. ................... 601/1 |
| 2005/0150056 | A1 | * | 7/2005 | Copete Vidal et al. ....... 8/115.51 |
| 2006/0127557 | A1 | | 6/2006 | Takata |
| 2006/0270745 | A1 | * | 11/2006 | Hunt et al. ................... 521/50.5 |
| 2007/0003510 | A1 | * | 1/2007 | Henry et al. ..................... 424/74 |
| 2007/0078065 | A1 | * | 4/2007 | Nuckols et al. ................ 508/136 |
| 2007/0134304 | A1 | * | 6/2007 | Aubrun-Sonneville et al. ............................. 424/443 |
| 2009/0155323 | A1 | * | 6/2009 | Sakai et al. .................... 424/401 |
| 2010/0166668 | A1 | * | 7/2010 | Wei et al. ..................... 424/9.43 |

FOREIGN PATENT DOCUMENTS

| | | |
|---|---|---|
| JP | 62-81432 | 4/1987 |
| JP | 62 81432 | 4/1987 |
| JP | 1987-081432 | 4/1987 |
| JP | 2 151693 | 6/1990 |
| JP | 2-151693 | 6/1990 |
| JP | 6 57293 | 3/1994 |
| JP | 6-057293 | 3/1994 |
| JP | 6-57293 | 3/1994 |
| JP | 6 239733 | 8/1994 |
| JP | 6-239733 | 8/1994 |
| JP | 6239733 | * 8/1994 |
| JP | 6-321728 | 11/1994 |
| JP | 6 321728 | 11/1994 |
| JP | 9-31492 | 2/1997 |
| JP | 2000 226322 | 8/2000 |
| JP | 2000-226322 | 8/2000 |
| JP | 2000-344801 | 12/2000 |
| JP | 2000 344801 | 12/2000 |
| JP | 2001 131054 | 5/2001 |
| JP | 2001-131054 | 5/2001 |
| JP | 2001131054 | * 5/2001 |
| JP | 2001 299340 | 10/2001 |
| JP | 2001-299340 | 10/2001 |
| JP | 2003 342162 | 12/2003 |
| JP | 2003-342162 | 12/2003 |
| JP | 2004-75762 | 3/2004 |
| JP | 2004 75762 | 3/2004 |
| JP | 2005 330372 | 12/2005 |
| JP | 2005-330372 | 12/2005 |
| JP | 2006-169300 | 6/2006 |
| JP | 2006 169300 | 6/2006 |

OTHER PUBLICATIONS

U.S. Appl. No. 12/374,099, filed Jan. 16, 2009, Takagi, et al.
Office Action issued Dec. 3, 2010, in China Patent Application No. 200780027579.9 (with English translation).
Office Action issued Sep. 9, 2011 in China Application No. 200780027579.9 (With English Translation).

* cited by examiner

*Primary Examiner* — Charles Boyer
(74) *Attorney, Agent, or Firm* — Oblon, Spivak, McClelland, Maier & Neustadt, L.L.P.

(57) ABSTRACT

The present invention relates to hydrogel particles containing bubbles and having a specific gravity of 0.7 to 1.00 and an average particle diameter of 50 to 500 μm, as well as a process for producing the same. The hydrogel particles may also contain hollow inorganic particles.

17 Claims, No Drawings

HYDROGEL PARTICLES

FIELD OF THE INVENTION

The present invention relates to hydrogel particles suitable for an object of washing.

BACKGROUND OF THE INVENTION

In recent years, various skin detergents of washout type (body detergents, facial washes, cold cream etc.) compounded with particles (scrub agent) have been marketed and used. This is because in addition to their new sense of use, there is an advantage that excess corneum (dirt) and dirt penetrating into pores of the skin, which are hardly removed with usual skin detergents, can be removed by the physical effect of the particles.

It is known that in consideration of problems such as skin irritation and rough dry skin, highly detergent and hypoallergenic scrub agents can be obtained by regulating the size and hardness of particles (JP-A 2-151693, JP-A 9-31492).

In detergents compounded with a scrub agent with such regulated particle size and hardness, however, there remain problems in use such as foreign-body sensation at the time of massage, difficult washout after washing, and difficult removal of particles accidentally entering the eye, and there is an increasing need for particles with improvements thereto. JP-A 6-57293 discloses a detergent composition excellent in washout of particles after washing, which contains crosslinked polymer particles with a specific gravity of 1 or less consisting of (meth)acrylate monomers.

Meanwhile, JP-A 62-81432 discloses a water-soluble polymer molding which contains bubbles and has a specific gravity of less than 1, and it is described therein that the water-soluble polymer molding, when used as a bath agent, has unique properties as a bath agent without submerging. This polymer molding is obtained by mixing a water-soluble polymer compound with an aqueous solution containing a bubble-regulating agent and then incorporating bubbles into the mixture, followed by molding into a sheet or the like and subsequent drying thereof, and when used, the polymer molding itself dissolves in water (water at 40° C.).

SUMMARY OF THE INVENTION

The present invention provides hydrogel particles which contain bubbles and have a specific gravity of 0.7 to 1.00 and an average particle diameter of 50 to 500 μm.

The invention provides a process for producing the above shown hydrogel particles, which includes stirring an aqueous solution containing a gel-former and a bubble-regulating agent to form a bubble-containing hydrogel and then forming it into particles.

The present invention provides use of the above shown hydrogel particles or hydrogel particles obtained by the above shown process as a scrub agent.

DETAILED DESCRIPTION OF THE INVENTION

The particles disclosed in JP-A 6-57293 are hydrophobic crosslinked polymer particles, and the adhesion and aggregation of the particles easily occur in water, so their apparent particle diameters would be increased.

The present invention provides hydrogel particles which have high detergency, are excellent in sense of use, and can be easily removed from the eye or skin after washing.

The present inventors found that hydrogel is allowed to contain bubbles to make its specific gravity equal to or lower than that of water or eyewater and further formed into particles having an average particle diameter of 50 to 500 μm, whereby hydrogel particles having high detergency, being excellent in sense of use, show less adhesion and aggregation among the particles in an aqueous system, and can be easily removed from the eye or skin after washing.

The present inventors found that hydrogel is allowed to contain hollow inorganic particles to make its specific gravity equal to or lower than that of water or eyewater, whereby hydrogel particles having high detergency, being excellent in sense of use, show less adhesion and aggregation among the particles in an aqueous system, and can be easily removed from the eye or skin after washing.

The hydrogel particles of the present invention are safer hydrogel particles which are excellent in physical washing effect, are very low in irritation and damage to the surface of an object of washing, for example, the skin, scalp etc., are also excellent in feel at the time of washing, and can be easily removed from the eye, skin etc. after washing.

The present invention relates to hydrogel particles which have excellent detergency and massage effect on an object of washing and are extremely excellent in washout with rinsing water or eyewater.

The hydrogel particles of the present invention are excellent in physical detergency, are made extremely excellent in washout with rinsing water or eyewater by making the specific gravity of the hydrogel particles equal to or lower than that of water or eyewater, and are useful as in detergent compositions etc.

The hydrogel particles of the present invention are hydrogel particles comprising bubbles and hydrogel and having a specific gravity of 0.7 to 1.00 and an average particle diameter of 50 to 500 μm.

The "hydrogel" in the present invention is gel formed by gelling with a gel-former with water as a solvent, and gelling is generated not by reaction for example with potassium ions, calcium ions etc., but by sol-gel thermal reversibility such as in the case where the gel-former is agar.

The shape of the hydrogel particles of the present invention is not particularly limited, and the shape of the particles is preferably spherical or elliptical. From the viewpoint of conferring scrub feel, the average particle diameter of the hydrogel particles of the present invention is 50 μm or more, preferably 60 μm or more. To reduce anxiety about entrance of the particles into the eye and to reduce uncomfortable feeling and skin irritation, the average particle diameter is 500 μm or less, preferably 400 μm or less.

In the present invention, the average particle diameter of the hydrogel particles was determined by observing the particles with a low-power zoom lens (VH-6300 (main body) manufactured by Keyence Corporation, VH-Z05 (CCD camera lens) manufactured by Keyence Corporation) and comparing the particle diameters of randomly selected 10 particles with a scale followed by proportional calculation.

From the viewpoint of easy removal form the skin, eye etc. at the time of washout and of reduction in foreign-body sensation, the specific gravity of the hydrogel particles of the present invention is 1.00 or less, preferably less than 1.00, more preferably 0.99 or less, even more preferably 0.98 or less. From the viewpoint of conferring suitable strength on the hydrogel particles, the specific gravity is 0.7 or more, preferably 0.8 or more, more preferably 0.85 or more.

In the present invention, the specific gravity of the hydrogel particles was determined by preparing arbitral ethanol aqueous solutions at 25° C. described in "Kagaku Binran" (Handbook of Chemistry) (revised 4th edition, page II-12, edited by the Chemical Society of Japan and published by Maruzen Co., Ltd.) and then measuring the hydrogel particles floating on the various different ethanol aqueous solutions.

The hydrogel particles of the present invention are preferably hydrophilic hydrogel particles containing a gel-former derived from a natural polymer compound. The gel-former derived from a natural polymer compound includes, for example, agar, gelatin, gum arabic, quince seed mucous substance, tragacanth gum, guar gum, karaya gum, locust bean gum, glucomannan, pectin, galactan, pullulan, xanthan gum, casein, casein potassium salt, casein sodium salt, sodium chondroitin sulfate, starch-based semisynthetic polymer compounds (for example, carboxymethyl starch, methylhydroxypropyl starch, methylhydroxymethyl starch etc.) and dextrin, among which agar is preferable. These gel-formers can be used alone or as a mixture of two or more thereof. From the viewpoint of achieving the effect of the present invention, agar is more preferable and may be used more preferably as the major component to constitute the hydrogel particles.

From the viewpoint of feel during use in application to cosmetics etc., the jelly strength of agar is preferably 147 kPa (1500 g/cm$^2$) or less, more preferably 19.6 kPa (200 g/cm$^2$) to 127 kPa (1300 g/cm$^2$). The jelly strength can be determined by a chilled-water-system method. Specifically, the jelly strength can be determined by producing a 1.5 percent by weight aqueous solution of the gel-former, leaving the aqueous solution at 20° C. for 15 hours to coagulate gel, applying a loading with a chilled-water-system jelly strength measuring instrument (manufactured by KIYA Corporation) and determining, as the jelly strength, the maximum weight (g) per cm$^2$ of the surface area of the gel capable of enduring the loading for 20 seconds at 20° C.

From the viewpoint of formation of particles, the gelling temperature of the hydrogel is preferably 30° C. or more, more preferably 35° C. or more. From the viewpoint of maintaining the particle shape by preventing the hydrogel from being melted during washing and during incorporation into cosmetics etc., the melting point of the hydrogel is preferably 50° C. or more, more preferably 60° C. or more.

From the viewpoint of excellent feel during use upon application to cosmetics etc. and of preventing disintegration of the hydrogel particles during washing and during incorporation into cosmetics etc., the content of the gel-former in the hydrogel particles of the present invention is preferably 0.1 to 8.0 percent by weight, more preferably 0.3 to 7.0 percent by weight, even more preferably 0.4 to 6.0 percent by weight, further more preferably 0.5 to 5.0 percent by weight.

The hydrogel particles of the present invention contain bubbles, and for allowing the hydrogel particles to contain bubbles, a bubble-regulating agent is preferably used at the time of production of the hydrogel particles. As the bubble-regulating agent, various surfactants can be used, and at least one member selected from an anionic surfactant and a nonionic surfactant is preferable. The anionic surfactant includes fatty acid salts, phosphates, acylated amino acids and sulfosuccinic acids. The nonionic surfactant includes alkyl saccharides, ethylene oxide addition-type surfactants etc. These surfactants can be used alone or as a mixture of two or more thereof, and are preferably anionic surfactants, more preferably fatty acid salts and phosphates, even more preferably fatty acid salts, particularly for the stability and safety of bubbles or fineness of bubbles. The fatty acid salts are preferably alkali metal salts of C8 to C24 fatty acids.

From the viewpoint of obtaining hydrogel particles with a specific gravity of 0.7 to 1.00, the content of the bubble-regulating agent in the hydrogel particles of the present invention is preferably 0.5 to 5.0 percent by weight, more preferably 1.0 to 5.0 percent by weight.

The hydrogel particles of the present invention may also contain water-soluble organic compounds such as sugars, polyhydric alcohols, water-soluble polymer compounds and water-soluble perfumes described in JP-A 2000-126586, in addition to the components described above.

The hydrogel particles of the present invention can be produced by mixing and stirring an aqueous solution containing a gel-former and a bubble-regulating agent to prepare a bubble-containing hydrogel and then forming it into particles.

A method of stirring an aqueous solution containing a gel-former and a bubble-regulating agent is not particularly limited, and bubbles can be easily contained in the hydrogel by a stirring method known in the art. For example, a gel-former and an aqueous solution containing a bubble-regulating agent are treated with a usual stirrer, disperser etc. By suitably selecting the amount of the bubble-regulating agent and treatment conditions of a stirrer or disperser, bubbles are contained such that the specific gravity of the hydrogel becomes 1 or less. As used herein, the term "specific gravity" refers to the ratio of the density of hydrogel to that of distilled water at 4° C. The temperature at which bubbles are contained in hydrogel is a temperature at which hydrogel is not solidified, for example 60 to 100° C., particularly preferably 70 to 90° C.

The hydrogel thus allowed to contain bubbles can be formed into particles by a known method to give the hydrogel particles of the present invention. The method of forming the hydrogel into particles includes, for example, a general falling-drop method, spray method etc.

The falling-drop method is a method wherein bubble-containing hydrogel is discharged through a pore, the discharged hydrogel is formed into droplets by its surface tension or interfacial tension, and the droplets are cooled and solidified in a gaseous phase such as air or in a liquid phase such as cooling oil to produce hydrogel particles. From the viewpoint of producing hydrogel particles having a uniform particle diameter, the hydrogel discharged through a pore is preferably vibrated.

The spray method is a method wherein bubble-containing hydrogel is sprayed through a spray nozzle into a gaseous phase and is simultaneously formed by its surface tension or interfacial tension into droplets, and the droplets are solidified by cooling in a gaseous phase to produce hydrogel particles.

In both the falling-drop method and spray method, the temperature of the bubble-containing hydrogel at the time of discharging and spraying is preferably a temperature of from the gelling temperature to 100° C. From the viewpoint of easy production of spherical particles excellent in appearance, the temperature of the bubble-containing hydrogel is preferably a temperature of the gel temperature +10° C. or more, more preferably a temperature of the gel temperature +20° C. or more. The upper limit of this temperature is 100° C. that is the boiling point of water. On the other hand, the temperature at which the hydrogel is cooled to form particles is preferably 0 to 30° C., more preferably 0 to 20° C.

The distance in which the hydrogel particles drop for cooling is preferably 1 to 10 mm, more preferably 1 to 5 m.

If necessary, the hydrogel particles of the present invention can be compounded with a wide variety of other components depending on their applications. For example, the hydrogel particles can be compounded with a humectant, a detergent, a perfume, a dye, an antioxidant, a preservative etc. Besides, the hydrogel particles can also be compounded with a UV absorber, an antibacterial agent etc.

The hydrogel particles of the present invention can be used widely in skin detergents such as facial washes, body detergents and solid soap, shampoos, scalp detergents, dishwashing detergents, detergents for contact lens, toothpastes and hair growth tonics, as well as massage agents.

The hydrogel particles of the present invention preferably contain hollow inorganic particles as bubbles. The hydrogel particles may be those having a specific gravity of 1.00 or less. Hereinafter, this embodiment is described in detail.

The hollow inorganic particles used in the present invention are particles which are formed from an inorganic material and have a cavity in the center. This cavity may be filled with an inert gas etc.

The hollow inorganic particles used in the present invention are preferably hydrophilic hollow inorganic particles, more preferably hollow glass particles, having hydrophilic groups such as a hydroxyl group, silicate group, sulfate group and ammonium group thereon. The hollow glass particles include hollow silicate glass, hollow borosilicate glass, etc. The volume-average particle diameter of the hollow inorganic particles is preferably 50 μm or less, more preferably 3 to 40 μm. The volume-average particle diameter of the hollow inorganic particles can be determined by a laser diffraction particle size distribution meter.

The specific gravity of the hollow inorganic particles is preferably 0.95 or less, more preferably 0.1 to 0.8.

The hollow inorganic particles used in the present invention can be commercial products, and the commercial products include, for example, hollow glass particles (trade name: Fuji Balloon H30, H35, H40, S-35, S-40, S-45) manufactured by Fuji Silysia Chemical Ltd. and the hollow glass beads manufactured by Suzuki-Oil Co., Ltd.

From the viewpoint of feel at the time of washing, the content of the hollow inorganic particles in the hydrogel particles of the present invention is preferably 0.1 to 35 percent by weight, more preferably 0.5 to 25 percent by weight.

The shape of the hydrogel particles of the present invention is not particularly limited, and may be spherical, elliptical, amorphous etc., preferably spherical or elliptical. From the viewpoint of giving scrub feel, the average particle diameter of the hydrogel particles of the present invention is preferably 50 μm or more, more preferably 60 μm or more. To reduce anxiety about entrance of the particles into the eye and to reduce uncomfortable feeling and skin irritation, the average particle diameter is 500 μm or less, preferably 450 μm or less, more preferably 400 μm or less.

From the viewpoint of particle shape, the gelling temperature of the hydrogel is preferably 30° C. or more, more preferably 35° C. or more. From the viewpoint of maintaining the particle shape by preventing the hydrogel from being melted during washing and during incorporation into cosmetics etc., the melting point of the hydrogel is preferably 50° C. or more, more preferably 60° C. or more.

The process for producing the hydrogel particles of the present invention is not particularly limited, and for example, the hydrogel particles can be produced by mixing an aqueous solution containing a gel-former under stirring, then adding hollow inorganic particles to prepare hydrogel containing the hollow inorganic particles, and converting the hydrogel into particles.

The method of stirring an aqueous solution containing a gel-former is not particularly limited, and the aqueous solution can be stirred and mixed with a stirrer or disperser known in the art. The temperature at which the aqueous solution is stirred and mixed is a temperature at which hydrogel is not solidified, for example 60 to 100° C., particularly preferably 70 to 90° C.

The hollow inorganic particle-containing hydrogel can be converted into particles by a known method to give the hydrogel particles of the present invention. The method of converting the hydrogel into particles is not limited, but includes, for example, a general falling-drop method, spray method etc.

The hollow inorganic particle-containing hydrogel can be produced by the general falling-drop method or spray method similarly as described above.

In both the falling-drop method and spray method, the temperature of the hydrogel at the time of discharging or spraying is preferably a temperature of from the gelling temperature to 100° C. From the viewpoint of easy production of spherical particles excellent in appearance, the temperature of the hydrogel at the time of discharging or spraying is preferably a temperature of the gel temperature +10° C. or more, more preferably a temperature of the gel temperature +20° C. or more. The upper limit of this temperature is 100° C. that is the boiling point of water. On the other hand, the temperature at which the hydrogel is cooled to form particles is preferably 0 to 30° C., more preferably 0 to 25° C. The distance in which the hydrogel particles drop for cooling is the same as described above.

EXAMPLES

Hereinafter, the present invention is described by reference to the Examples. The Examples are merely illustrative of the present invention and not intended to limit the present invention.

Unless otherwise specified, the terms "%" and "parts" in the Examples refer to "% by weight" and "parts by weight" respectively.

Example 1

As a gel-former consisting of a natural polymer compound, 30.0 g agar powder (AX-200, manufactured by Ina Food Industry Co., Ltd.) was weighed out and introduced into a 1000-mL separable flask, and 870.0 g of ion exchanged water was introduced into the flask, and then the gel-former was dissolved by heating at 80 to 90° C. under stirring with an anchor type stirrer, and then 96.6 g of 10% aqueous potassium laurate and 3.4 g of 10% aqueous potassium stearate were added as the bubble-regulating agent, to give 1000 g liquid mixture.

Then, this liquid mixture was stirred at 10000 rpm with an emulsifier (trade name: T. K. Homomixer MARK II 2.5 model, manufactured by Tokushu Kika Kogyo Co., Ltd.) for 2 minutes to prepare bubble-containing hydrogel.

The bubble-containing hydrogel was sprayed at a flow rate of 12 kg/hr through a spray nozzle (hollow-cone nozzle K-008, manufactured by H. Ikeuchi & Co., Ltd.) at a height of 3.4 m into a gaseous phase at 25° C., and particles settling in the gaseous phase were recovered to give hydrogel particles. The average particle diameter of the resulting hydrogel particles was 234 μm, and the specific gravity thereof was 0.96.

Examples 2 to 4

Hydrogel particles were obtained by the same preparation method as in Example 1 except that the kind of the bubble-regulating agent was changed as shown in Table 1.

Comparative Example 1

Hydrogel particles were obtained by the same preparation method as in Example 1 except the kind and amount of the bubble-regulating agent were changed.

Comparative Example 2

Hydrogel particles were obtained by the same preparation method as in Example 1 except the bubble-regulating agent was not added.

The average particle diameters and specific gravities of the hydrogel particles obtained in Examples 1 to 4 and Comparative Example 1 to 2 were measured by the methods described above. The detergency and washout property were evaluated by the following methods. The results are shown in Table 1.

<Method of Evaluating Detergency>

(1) Preparation of Detergent Solutions

A mixture of 10% potassium laurate (Wako Pure Chemical Industries, Ltd.), 20% hydrogel particles obtained in each of Examples 1 to 4 and Comparative Examples 1 to 2, and 70% ion exchanged water was uniformly dissolved and dispersed at room temperature.

(2) Evaluation of Detergency

Model sebum with the following composition having carbon black dispersed therein was prepared, and 20 mg of the model sebum was applied within a circle of $\phi$25 mm on artificial leather, and 200 mg of the detergent solution described above was dropped onto the part onto which the model sebum had been applied, and then the artificial leather was subjected to massage washing 20 times, then rinsed with tap water and air-dried.

The chromaticity (Lab) of the arm at each time point in the washing procedure, that is, before treatment (before application of the model sebum), before washing (after application of the model sebum) and after washing (after rinsing and air-drying) was measured with calorimeter CR-200 (manufactured by Minolta), and the chromaticity before the treatment was used as the reference value, and from the color difference between the colors before and after washing, the degree of washing of the model sebum was calculated according to the following equation. The detergency was evaluated under the following criteria by using relative value assuming that the degree of washing with 10% aqueous potassium laurate (in the absence of the hydrogel particles) was 1.

Degree of detergency (%)=(1−(color difference after washing/color difference before washing))×100

● Evaluation criteria for detergency x: Degree of washing<degree of washing in the absence of hydrogel particles Δ: Degree of washing in the absence of hydrogel particles≦degree of washing<[degree of washing in the absence of hydrogel particles×1.1]

○: [Degree of washing in the absence of hydrogel particles× 1.1]≦degree of washing <Method of Evaluating Washout Property>

0.1 g of 20% aqueous solution of hydrogel particles was left on black artificial leather. Then, the black artificial leather was declined at 10°, and then 2 g ion exchanged water was dropped onto it through a dropper. The state of dropping was observed with a stereoscopic microscope (SM2-2T) manufactured by Nikon Corporation, and 10 seconds after dropping, the number of hydrogel particles remaining in the visual field (about 1 cm) was counted to evaluate washout property under the following criteria:

x: 10 or more hydrogel particles were recognized in the visual field.

Δ: 1 to 9 hydrogel particles were recognized in the visual field.

○: No hydrogel particle was recognized in the visual field.

| Model sebum composition | |
|---|---|
| (Model sebum) | |
| Squalane (manufactured by Wako Pure Chemical Industries, Ltd.) | 9.0 parts |
| Myristyl myristate (trade name: Exepearl MY-M, manufactured by Kao Corporation) | 24.0 parts |
| Cotton seed oil (manufactured by Kanto Kagaku Co., Ltd.) | 47.0 parts |
| Cholesterol (manufactured by Wako Pure Chemical Industries, Ltd.) | 2.0 parts |
| Cholesterol palmitate (manufactured by Tokyo Chemical Industry Co., Ltd.) | 2.0 parts |
| Laurie acid (trade name: LUNAC L-98, manufactured by Kao Corporation) | 0.2 parts |
| Myristic acid (trade name: LUNAC MY-98, manufactured by Kao Corporation) | 2.5 parts |
| Palmitic acid (trade name: LUNAC P-95, manufactured by Kao Corporation) | 6.0 parts |
| Stearic acid (trade name: LUNAC P-98, manufactured by Kao Corporation) | 0.9 part |
| Oleic acid (manufactured by Wako Pure Chemical Industries, Ltd.) | 6.4 parts |
| Total | 100 parts |
| (Marker) | |
| Carbon black (manufactured by Mitsubishi Chemical Corporation) | 5 parts |

TABLE 1

| | | Bubble-regulating agent | | Average particle diameter (μm) | Particle specific gravity | Detergency | Washout property |
|---|---|---|---|---|---|---|---|
| | | Kind | Containing amount (percent by weight*[2]) | | | | |
| Example | 1 | K laurate/ K stearate | 1.0 | 234 | 0.96 | ○ | ○ |
| | 2 | MAP-115K*[1] | 1.0 | 239 | 0.98 | ○ | ○ |
| | 3 | Na laurate | 1.0 | 211 | 0.96 | ○ | ○ |
| | 4 | Na stearate | 1.0 | 88 | 0.92 | ○ | ○ |
| Comparative example | 1 | MAP-115K*[1] | 0.1 | 250 | 1.02 | ○ | X |
| | 2 | None | — | 201 | 1.02 | ○ | X |

*[1]30% aqueous solution of a potassium monoalkyl phosphate having alkyl chain lengths with an alkyl group composition of $C_{11}/C_{13}/C_{15} = 48/31/21$ (weight ratio).
*[2]Weight % based on the total amount of the hydrogel particles

Example 5

As a gel-former consisting of a natural polymer compound, 30.0 g agar powder (UM-11KS, manufactured by Ina Food Industry Co., Ltd.) was weighed out and introduced into a 1000-mL separable flask, and 940.0 g ion exchanged water was introduced into the flask, and then the gel-former was dissolved by heating at 80 to 90° C. under stirring with an anchor type stirrer. Then, 30.0 g of hollow glass particles (Fuji Balloon H30, that is, spherical hollow borosilicate glass particles with a volume-average particle diameter of 40 μm and a true specific gravity of 0.30, manufactured by Fuji Silysia Chemical Ltd.) was added to the solution to give 1000 g liquid mixture as hollow glass-containing hydrogel.

Then, this hollow glass-containing hydrogel was sprayed at a flow rate of 12 kg/hr through a spray nozzle (hollow-cone nozzle K-008, manufactured by H. Ikeuchi & Co., Ltd.) at a height of 3.4 m into a gaseous phase at 25° C., and particles settling in the gaseous phase were recovered to give hydrogel particles. The average particle diameter of the resulting hydrogel particles was 320 μm, and the specific gravity thereof was 0.94.

Example 6

Hydrogel particles were obtained in the same preparation method as in Example 5 except that 30.0 g hollow glass beads (volume-average particle diameter 10 μm, specific gravity 0.2) manufactured by Suzuki-Oil Co., Ltd. were used as the hollow glass particles.

Comparative Example 3

Hydrogel particles were obtained in the same preparation method as in Example 5 except that 30.0 g glass beads (volume-average particle diameter 8.5 μm, specific gravity 1.1) manufactured by Fuji Silysia Chemical Ltd. were used in place of the hollow glass particles.

Comparative Example 4

Hydrogel particles were obtained in the same preparation method as in Example 5 except that 30.0 g crosslinked metal polyacrylate particles (trade name: Polymer SK, volume-average particle diameter of 100 μm, manufactured by Kao Corporation) were used in place of the hollow glass particles.

The average particle diameters and specific gravities of the hydrogel particles obtained in Examples 5 to 6 and Comparative Example 3 to 4 were measured by the methods described above. The detergency and washout property were evaluated by the following methods. The results are shown in Table 2.

TABLE 2

| | | Added particles | | Hydrogel particle | | Result of evaluation | |
|---|---|---|---|---|---|---|---|
| | | Kind | Added amount (%*[1]) | Average particle diameter (μm) | Gravity | Detergeny | Washout property |
| Example | 5 | Hollow glass particles (Fuji Balloon H30) | 3.0 | 320 | 0.94 | ○ | ○ |
| | 6 | Hollow glass beads (manufactured by Suzuki-Oil Co., Ltd.) | 3.0 | 450 | 0.96 | ○ | ○ |
| Comparative example | 3 | Glass beads | 3.0 | 280 | 1.03 | ○ | X |
| | 4 | Crosslinked polyacrylate particles | 3.0 | 350 | 1.04 | ○ | X |

*[1]Weight % based on the total amount of hydrogel particles

The invention claimed is:

1. A method for cleansing the skin comprising scrubbing the skin with a scrub agent comprising hydrogel particles comprising bubbles and having a specific gravity of 0.7 to 1.00 and an average particle diameter of 50 to 500 μm, wherein the hydrogel particles are obtained by a process comprising:
stirring an aqueous solution comprising 0.1 to 8.0 percent by weight of a gel-former and 0.5 to 5.0 percent by weight of a bubble-regulating agent to form a bubble-containing hydrogel and water, and then discharging the bubble-containing hydrogel through a pore into a gaseous phase or a liquid phase to form bubble-containing hydrogel particles, or spraying the bubble-containing hydrogel through a spray nozzle into a gaseous phase to form bubble-containing hydrogel particles.

2. The method according to claim 1, wherein the gel-former is selected from the group consisting of agar, gelatin, gum arabic, quince seed mucous substance, tragacanth gum, guar gum, karaya gum, locust bean gum, glucomannan, pectin, galactan, pullulan, xanthan gum, casein, casein potassium salt, casein sodium salt, sodium chondroitin sulfate, dextrin and starch-based semi-synthetic polymer compounds.

3. The method according to claim 1, wherein the bubble-regulating agent is selected from the group consisting of an anionic surfactant and a nonionic surfactant.

4. The method according to claim 3, wherein the bubble-regulating agent is an anionic surfactant selected from the group consisting of a fatty acid salt, a phosphate, an acylated amino acid and a sulfosuccinic acid.

5. The method according to claim 3, wherein the bubble-regulating agent is a nonionic surfactant selected from the group consisting of an alkyl saccharide and an ethylene oxide addition-type surfactant.

6. The method according to claim 1, wherein the hydrogel has a gelling temperature of 30° C. or more.

7. A method for cleansing the skin comprising scrubbing the skin with a scrub agent comprising hydrogel particles comprising hollow inorganic particles and having a specific gravity of 0.7 to 1.00 and an average particle diameter of 50 to 500 μm, wherein the hydrogel particles are obtained by a process comprising:
stirring an aqueous solution comprising 0.1 to 8.0 percent by weight of a gel-former and 0.1 to 35 percent by weight of one or more hollow inorganic particles to form a hollow inorganic particle-containing hydrogel, and then discharging the hollow inorganic particle-containing hydrogel through a pore into a gaseous phase or a liquid phase to form hollow inorganic particle-containing hydrogel particles, or spraying the hollow inorganic particle-containing hydrogel through a spray nozzle into a gaseous phase to form hollow inorganic particle-containing hydrogel particles.

8. The method according to claim 7, wherein the hollow inorganic particles are hollow glass particles.

9. The method according to claim 7, wherein the gel-former is selected from the group consisting of agar, gelatin, gum arabic, quince seed mucous substance, tragacanth gum, guar gum, karaya gum, locust bean gum, glucomannan, pectin, galactan, pullulan, xanthan gum, casein, casein potassium salt, casein sodium salt, sodium chondroitin sulfate, dextrin and starch-based semi-synthetic polymer compounds.

10. The method according to claim 7, wherein the hydrogel has a gelling temperature of 30° C. or more.

11. The method according to claim 1, wherein the hydrogel particles are hydrophilic hydrogel particles containing a gel-former derived from a natural polymer compound.

12. The method according to claim 7, wherein the hydrogel particles are hydrophilic hydrogel particles containing a gel-former derived from a natural polymer compound.

13. The method according to claim 7, wherein the hydrogel particles comprise at least one bubble-regulating agent selected from the group consisting of an anionic surfactant and a nonionic surfactant.

14. The method according to claim 1, wherein the hydrogel particles are spherical or elliptical.

15. The method according to claim 7, wherein the hydrogel particles are spherical or elliptical.

16. The method according to claim 1, wherein the gel former is agar.

17. The method according to claim 7, wherein the gel former is agar.

* * * * *